(12) United States Patent
Plojoux et al.

(10) Patent No.: US 10,966,461 B2
(45) Date of Patent: Apr. 6, 2021

(54) HEATING ELEMENT MODULE FOR AN AEROSOL-GENERATING DEVICE

(71) Applicant: Philip Morris Products S.A., Neuchatel (CH)

(72) Inventors: Julien Plojoux, Geneva (CH); Dani Ruscio, Cressier (CH)

(73) Assignee: Philip Morris Products S.A., Neuchatel (CH)

( * ) Notice: Subject to any disclaimer, the term of this patent is extended or adjusted under 35 U.S.C. 154(b) by 306 days.

(21) Appl. No.: 15/544,553

(22) PCT Filed: Mar. 22, 2016

(86) PCT No.: PCT/EP2016/056292
§ 371 (c)(1),
(2) Date: Jul. 19, 2017

(87) PCT Pub. No.: WO2016/156121
PCT Pub. Date: Oct. 6, 2016

(65) Prior Publication Data
US 2018/0007971 A1 Jan. 11, 2018

(30) Foreign Application Priority Data

Mar. 31, 2015 (EP) ..................................... 15162071
Jun. 19, 2015 (EP) ..................................... 15173021

(51) Int. Cl.
*A24F 47/00* (2020.01)
*A24F 40/40* (2020.01)
(Continued)

(52) U.S. Cl.
CPC ............ *A24F 47/008* (2013.01); *A24F 40/40* (2020.01); *F22B 1/284* (2013.01); *A61M 11/042* (2014.02)

(58) Field of Classification Search
CPC ... A24F 47/008; A61M 11/042; A61M 15/06; A61M 2205/8206; F22B 1/284
(Continued)

(56) References Cited

U.S. PATENT DOCUMENTS 4,966,171 A * 10/1990 Serrano ................ A24B 15/165
131/194
5,144,962 A * 9/1992 Counts ................. A24F 47/008
131/194

(Continued)

FOREIGN PATENT DOCUMENTS

CN 102665459 A 9/2012
CN 104023574 A 9/2014
(Continued)

OTHER PUBLICATIONS

Extended European Search Report dated Aug. 20, 2015 in Patent Application No. 15173021.5.
(Continued)

*Primary Examiner* — Dana Ross
*Assistant Examiner* — Michael S. Poetzinger
(74) *Attorney, Agent, or Firm* — Oblon, McClelland, Maier & Neustadt, L.L.P.

(57) ABSTRACT

A heating element module for an aerosol-generating device is provided, including an elongate heating element having a heating portion; a heating element mount, wherein the heating element extends substantially perpendicularly from a first surface of the heating element mount; and first and second projections extending substantially perpendicularly from the first surface of the heating element mount and abutting first and second sides of the heating element. An aerosol-generating device incorporating the heating element module is also provided.

10 Claims, 3 Drawing Sheets

(51) Int. Cl.
*F22B 1/28* (2006.01)
*A61M 11/04* (2006.01)

(58) Field of Classification Search
USPC .......................................... 392/394–398, 404
See application file for complete search history.

(56) References Cited

U.S. PATENT DOCUMENTS

| | | | |
|---|---|---|---|
| 10,582,729 B2 * | 3/2020 | Lord | ..................... A24F 47/008 |
| 2012/0260927 A1 | 10/2012 | Liu | |
| 2014/0060554 A1 | 3/2014 | Collett et al. | |
| 2014/0366898 A1 | 12/2014 | Monsees et al. | |
| 2014/0373856 A1 | 12/2014 | Zuber et al. | |
| 2015/0163859 A1 | 6/2015 | Schneider et al. | |
| 2018/0235284 A1 * | 8/2018 | Lord | ..................... A24F 47/008 |

FOREIGN PATENT DOCUMENTS

| | | | | |
|---|---|---|---|---|
| CN | 104470387 A | 3/2015 | | |
| EP | 2 316 286 A1 | 5/2011 | | |
| JP | 61-71984 U | 5/1986 | | |
| JP | 2015-508287 A | 3/2015 | | |
| WO | WO 2013/098409 A1 | 7/2013 | | |
| WO | WO-2013098395 A1 * | 7/2013 | ........... | A24F 47/002 |
| WO | WO-2013098411 A1 * | 7/2013 | ........... | A24F 47/008 |
| WO | WO 2014/012905 A1 | 1/2014 | | |
| WO | WO 2014/102092 A1 | 7/2014 | | |

OTHER PUBLICATIONS

International Search Report and Written Opinion dated Jun. 13, 2016 in PCT/EP2016/056292, filed Mar. 22, 2016.
Combined Chinese Office Action and Search Report dated Oct. 11, 2019, in Patent Application No. 201680015387.5, 15 pages (with English translation).
Japanese Office Action dated Apr. 28, 2020 in Patent Application No. 2017-549282 (with English translation), 7 pages.
Combined Chinese Office Action and Search Report dated Aug. 13, 2020 in corresponding Chinese Patent Application No. 201680015387.5 (with English Translation and English Translation of Category of Cited Documents), 18 pages.
Office Action dated Aug. 31, 2020 in corresponding Japanese Patent Application No. 2017-549282 (with English Translation), 4 pages.

* cited by examiner

HEATING ELEMENT MODULE FOR AN AEROSOL-GENERATING DEVICE

The present invention relates to a heating element module suitable for use in an aerosol-generating device or aerosol-generating system, and to an aerosol-generating device or system incorporating such a heating element module. In particular, the invention relates to a heating element module for heating an aerosol-generating article having a solid aerosol-forming substrate.

There is increasing demand for handheld aerosol-generating devices that are able to deliver aerosol for user inhalation. One particular area of demand is for heated smoking devices in which an aerosol-forming substrate is heated to release volatile flavour compounds, without combustion of the aerosol-forming substrate. The released volatile compounds are conveyed within an aerosol to the user.

Any aerosol-generating device that operates by heating an aerosol-forming substrate must include a heating assembly. A number of different types of heating assembly have been proposed for different types of aerosol-forming substrate.

One type of heating assembly that has been proposed for heated smoking devices operates by inserting a heater into a solid aerosol-forming substrate, such as a plug of tobacco. This arrangement allows the substrate to be heated directly and efficiently. But there are number of technical challenges with this type of heating assembly, including meeting requirements for small size, robustness, low manufacturing cost, sufficient operating temperatures and effective localisation of generated heat.

Heated aerosol-generating articles comprising tobacco for generation of an aerosol by heating rather than burning are known in the art. Tobacco used as part of an aerosol-forming substrate in heated aerosol-generating articles is designed to produce an aerosol when heated rather than when burned. Aerosol-generating devices for heating such aerosol-generating articles may have a heating element which is insertable into the tobacco of the aerosol-generating article to improve the heat transfer.

It would be desirable to provide a robust, inexpensive, heating assembly for an aerosol-generating device that provides a localised source of heat for heating an aerosol-forming substrate.

According to a first aspect of the present invention, there is provided a heating element module for an aerosol-generating device comprising: an elongate heating element having a heating portion; a heating element mount, wherein the heating element extends substantially perpendicularly from a first surface of the heating element mount; and first and second projections extending substantially perpendicularly from the first surface of the heating element mount and abutting first and second sides of the heating element.

Advantageously, in use, providing first and second projections reduces the flexural deflection of the elongate heating element, and increases the resistance to failure, including fracture.

The portion of the heating element extending from the first surface of the heating element mount preferably has a length which is greater than its width which is greater than its thickness, the first and second sides of the heating portion being faces defined by the width and length.

The first and second projections preferably extend from the first surface of the heating element mount for a distance of between about 2 mm and about 10 mm along the length of the heating portion. More preferably, the first and second projections extend from the first surface of the heating element mount for a distance of between about 3 mm and about 6 mm along the length of the heating portion.

Each of the first and second projections preferably have a non-planar free surface. The free surface of the projection is defined as the surface of the projections not attached to the first surface of the heating element mount, and not abutting the heating element. The free surface is preferably tapered away from the heating element mount. The non-planar free surface of each of the first and second projections is spherical, for example, each projection may be a quarter of a sphere. The non-planar free surface may, thus, be described as a spherical portion. Alternatively, each non-planer free surface may be conical, for example, a half-cone. Each projection may be frusto-conical.

It may be preferable that at least a portion of the heating element mount is cone-shaped. Cone-shaped includes pyramid-shaped. The entire heating element mount may be cone shaped, with the apex of the cone pointing towards the heating portion of the heater.

When used in an aerosol-generating device, the heating element module having first and second projections with a non-planer free surface, may improve the airflow through an aerosol-generating article used with the device. The non-planar free surface enables a portion of an end of an aerosol-generating article to abut a leading edge of each projection, while maintaining an airflow pathway to the remainder of the end of the aerosol-generating article.

The portions of the first and second projections in abutting relationship to the first and second sides of the heating element may be arranged to freely slide relative to the heating element. In this way, the abutting interface between the first and second projections can accommodate different contraction and expansion rates of the heating element mount material and the heating element material.

As used herein, the term 'aerosol-forming substrate' relates to a substrate capable of releasing volatile compounds that can form an aerosol. Such volatile compounds may be released by heating the aerosol-forming substrate. An aerosol-forming substrate may conveniently be part of an aerosol-generating article or smoking article.

As used herein, the terms 'aerosol-generating article' and 'smoking article' refer to an article comprising an aerosol-forming substrate that is capable of releasing volatile compounds that can form an aerosol. For example, an aerosol-generating article may be a smoking article that generates an aerosol that is directly inhalable into a user's lungs through the user's mouth. An aerosol-generating article may be disposable. A smoking article comprising an aerosol-forming substrate comprising tobacco is referred to as a tobacco stick.

The heating element mount provides structural support to the heating element and allows it to be securely fixed within an aerosol-generating device. The heating element mount may comprise a polymeric material and advantageously is formed from a mouldable polymeric material, such as polyether ether ketone (PEEK). The use of a mouldable polymer allows the heating element mount to be moulded around the heating element and thereby firmly hold the heating element. It also allows the heating element mount to be produced with a desired external shape and dimensions in an inexpensive manner. The heater substrate may have mechanical features, such as lugs or notches, which enhance the fixing of the heating element mount to the heater. It is of course possible to use other materials for the heater mount, such as a ceramic material. Advantageously, the heater mount may be formed from a mouldable ceramic material.

The first and second projections may be integrally moulded with the heating element mount. The first and second projections may be formed on the heating element mount after the heating element is received in the mount. The heating element may be provided with a release agent to prevent the projection material from adhering to the heating element during formation.

The use of a polymer to hold the heating element means that the temperature of the heater in the vicinity of the heating element mount must be controlled to be below the temperature at which the polymer will melt burn or otherwise degrade. At the same time the temperature of the portion of the heater within the aerosol-forming substrate must be sufficient to produce an aerosol with the desired properties.

The heating portion may comprise a ceramic insulating substrate supporting tracks formed from an electrically conductive material. The heater substrate may be formed from a brittle material and the heater mount may provide support to prevent flexing and torsion of the heater. The heater substrate formed from an electrically insulating material, may be a ceramic material such as Zirconia or Alumina. The heater substrate may provide a mechanically stable support for the heating element over a wide range of temperatures and may provide a rigid structure suitable for insertion into an aerosol-forming substrate. The heater substrate may comprise a planar surface on which the heating element is positioned and a tapered end configured to allow for insertion into an aerosol-forming substrate. The heater substrate advantageously has a thermal conductivity of less than or equal to 2 Watts per metre Kelvin.

The heating element module preferably further comprises electrical contacts for supplying power to the heating portion extend from a second surface of the heating element mount.

The heating element may comprise portions formed from different materials. The heating element may comprise a first portion and a second portion configured such that, when an electrical current is passed through the heating element the first portion is heated to a higher temperature than the second portion, or vice-versa. The first portion of the heating element may be formed from a first material and the second portion of the heating element may be formed from a second material, wherein the first material has a greater electrical resistivity coefficient than the second material. For example, the first material may be Ni—Cr (Nickel-Chromium), platinum, tungsten or alloy wire and the second material may be gold or silver or copper. The dimensions of the first and second portions of the heater element may also differ to provide for a lower electrical resistance per unit length in the second portion.

In an electrically resistive heater, the heat produced by the heater is dependent on the resistance of the heating element. For a given current, the higher the resistance of the heating element the more heat is produced. It is desirable that most of the heat produced is produced by the first portion of the heating element. Accordingly it is desirable that the first portion of the heating element has a greater electrical resistance per unit length than the second portion of the heater element.

In one embodiment, the first portion of the heating element may be formed from material having a defined relationship between temperature and resistivity. This allows the heater to be used both to the heat the aerosol-forming substrate and to monitor temperature during use. Advantageously, the first portion has a greater temperature coefficient of resistance than the second portion. This ensures that the value of resistance of the heater element predominantly reflects the temperature of the first portion of the heater element. Platinum has been found to be a good choice for the first portion of the heater element.

The dimensions of the heater may be chosen to suit the application of the heating assembly, and it should be clear that the width, length and thickness of the heater may be selected independently of one another. In one embodiment the heater is substantially blade shaped and has a tapered end for insertion into an aerosol-forming substrate. The heater may have a total length of between about 15 mm and about 30 mm, and advantageously between about 20 mm and about 25 mm. The surface of the heater on which the heating element is positioned may have a width of between about 2 mm and about 10 mm, and advantageously between about 3 mm and about 6 mm. The heater may have a thickness of between about 0.2 mm and about 0.5 mm and preferably between 0.3 mm and 0.4 mm. The active heating area of the heater, corresponding to the portion of the heater in which the first portion of the heating element is positioned, may have a length of between 5 mm and 20 mm and advantageously is between 8 mm and 15 mm. The distance between the heater mount and the first portion of the heating element may be at least 2 mm and advantageously at least 2.5 mm. In a preferred embodiment the distance between the heater mount and the first portion of the heating element is 3 mm.

The heating element may further comprise a heater substrate, and the heating portion further comprising a first portion and a second portion configured such that, when an electrical current is passed through the heating portion the first portion is heated to a higher temperature than the second portion. The first portion of the heating portion is positioned on a heating area of the heater substrate, and the second portion of the heating portion is positioned on a holding area of the heater substrate. The heating element mount and the first and second projections are adjacent the holding area of the heater substrate.

Preferably, the second portion of the heating portion is longer than the first portion. That is, the second portion extends along a greater length of the heater than the first portion.

The second portion of the heating portion may have, for example, a length of between 12 mm and 20 mm. Length is determined with respect to the longitudinal dimension of the heater. The second portion of the heating portion may have a length about 13 mm or about 14 mm.

The first portion of the heating portion may have, for example, a length of between 8 mm and 12 mm. The first portion of the heating portion may have a length of about 10 mm or about 11 mm.

In preferred embodiments, the second portion of the heating portion may extend along 13.9 mm of the length of the heater, plus or minus 0.5 mm, and the first portion of the electrically resistive heating element may extend along 10.5 mm of the length of the heater, plus or minus 0.5 mm.

The first portion is heated to a higher temperature than the second portion as a result of the electrical current passing through the heating element. In one embodiment, the first portion of the heating element is configured to reach a temperature of between about 300 degrees C. and about 550 degrees C. in use. Preferably, the heating element is configured to reach a temperature of between about 320 degrees C. and about 350 degrees C.

In an electrically resistive heater, the heat produced by the heater is dependent on the resistance of the heating element. For a given current, the higher the resistance of the heating element the more heat is produced. It is desirable that most of the heat produced is produced by the first portion.

Accordingly it is desirable that the first portion of the heating element has a greater electrical resistance per unit length than the second portion of the heater element.

Advantageously, the heating element may comprise portions formed from different materials. The first portion of the heating element may be formed from a first material and the second portion of the heating element may be formed from a second material, wherein the first material has a greater electrical resistivity coefficient than the second material. For example, the first material may be Ni—Cr (Nickel-Chromium), platinum, tungsten or alloy wire and the second material may be gold or silver or copper. The dimensions of the first and second portions of the heater element may also differ to provide for a lower electrical resistance per unit length in the second portion.

The materials for the first and second portions of the heating element may be selected for their thermal properties as well as their electrical properties. Advantageously, the second portion of the heating element may have a low thermal conductivity, in order to reduce conduction of heat from the heating area to the heater mount. Accordingly, the choice of material for the second portion of the heating element may be a balance between high electrical conductivity and low thermal conductivity, at least in the region between the first portion of the heating element and the heater mount. In practice, gold has been found to be a good choice of material for the second portion of the heating element. Alternatively, silver may comprise the second portion material.

Advantageously, the second portion of the heating element may comprise two sections, each of the two sections being separately connected to the first portion of the heating element to define an electrical flow path from the one section of the second portion to the first portion and then to the other section of the second portion. The heater mount may surround both sections of the second portion. It is of course possible for the second portion to comprise more than two portions, each electrically connected to the first portion.

The heating element may comprise a third portion configured for electrical connection to power supply, wherein the third portion is positioned on an opposite side of the heater mount to the first portion of the heating element. The third portion may be formed from a different material to the first and second portions, and may be chosen to provide a low electrical resistance and good connection properties, for example, easily solderable. In practice, silver has been found to be a good choice for the third portion. Alternatively, gold may be used as the material for the third portion. The third portion may comprise a plurality of sections, each connected to a section of the second portion of the heating element.

According to a second aspect of the present invention, there is provided an aerosol-generating device comprising an elongate cavity for receiving an aerosol-generating article, and a heating element module as described herein. The heating portion of the heating element is arranged to extend into the cavity such that it is insertable into an aerosol-generating article received in the cavity.

As used herein, an 'aerosol-generating device' relates to a device that interacts with an aerosol-forming substrate to generate an aerosol. The aerosol-forming substrate may be part of an aerosol-generating article, for example part of a smoking article. An aerosol-generating device may be a smoking device that interacts with an aerosol-forming substrate of an aerosol-generating article to generate an aerosol that is directly inhalable into a user's lungs thorough the user's mouth. An aerosol-generating device may be a holder.

The heating element mount may form a surface closing one end of the cavity.

The device is preferably a portable or handheld device that is comfortable to hold between the fingers of a single hand. The device may be substantially cylindrical in shape and has a length of between 70 and 120 mm. The maximum diameter of the device is preferably between 10 and 20 mm. In one embodiment the device has a polygonal cross section and has a protruding button formed on one face. In this embodiment, the diameter of the device is between 12.7 and 13.65 mm taken from a flat face to an opposing flat face; between 13.4 and 14.2 taken from an edge to an opposing edge (i.e., from the intersection of two faces on one side of the device to a corresponding intersection on the other side), and between 14.2 and 15 mm taken from a top of the button to an opposing bottom flat face.

The device may be an electrically heated smoking device.

The device may include other heaters in addition to the heating element module according to the first aspect. For example the device may include an external heater positioned around a perimeter of the cavity. An external heater may take any suitable form. For example, an external heater may take the form of one or more flexible heating foils on a dielectric substrate, such as polyimide. The flexible heating foils can be shaped to conform to the perimeter of the cavity. Alternatively, an external heater may take the form of a metallic grid or grids, a flexible printed circuit board, a moulded interconnect device (MID), ceramic heater, flexible carbon fibre heater or may be formed using a coating technique, such as plasma vapour deposition, on a suitable shaped substrate. An external heater may also be formed using a metal having a defined relationship between temperature and resistivity. In such an exemplary device, the metal may be formed as a track between two layers of suitable insulating materials. An external heater formed in this manner may be used to both heat and monitor the temperature of the external heater during operation.

The power supply may be any suitable power supply, for example a DC voltage source such as a battery. In one embodiment, the power supply is a Lithium-ion battery. Alternatively, the power supply may be a Nickel-metal hydride battery, a Nickel cadmium battery, or a Lithium based battery, for example a Lithium-Cobalt, a Lithium-Iron-Phosphate, Lithium Titanate or a Lithium-Polymer battery.

The control element may be a simple switch. The switch may be a puff activated switch, such as a microphone. Alternatively the control element may be electric circuitry and may comprise one or more microprocessors or microcontrollers.

In a third aspect of the invention, there is provided an aerosol-generating system comprising an aerosol-generating device according to the second aspect of the invention and one or more aerosol-forming articles configured to be received in the cavity of the aerosol-generating device. The aerosol-generating article includes an aerosol-forming substrate.

The aerosol-generating system may comprise a heated aerosol-generating article, the heated aerosol-generating article comprising a plurality of components including an aerosol-forming substrate assembled within a wrapper to form a rod having a mouth end and a distal end upstream from the mouth end. A hollow tube, which may have an external diameter of between 5 mm and 15 mm and a length of between 5 mm and 15 mm, may be disposed upstream from the aerosol-forming substrate within the wrapper. The heater of the aerosol-generating device is of sufficient length to extend through the lumen of the hollow tube and penetrate the aerosol-forming substrate when the heated aerosol-generating article is engaged with the aerosol-generating device.

The hollow tube may be rigid and may be formed from a substantially non-flammable material. As defined herein, a non-flammable material is a material that is difficult or impossible to ignite using a flame having a temperature of between 800° C. to 1700° C. and typically in the range of 800° C. to 1200° C. In general, any material that does not substantially release a toxic or otherwise harmful or undesirable compound in a temperature range between approximately 800° C. to 1200° C. or up to 1700° C. is within the substantially non-flammable materials contemplated herein.

A pierceable film may span one end of the hollow tube. The hollow tube has a proximal end and a distal end. The pierceable film may span the distal end of the hollow tube. The pierceable film may span the proximal end of the hollow tube. A hollow tube spanned by a pierceable film may protect the distal end of the rod from ignition in case a user applies a flame and draws on the mouth end of the article. The heat from the flame impinges the hollow tube, which is non-flammable. The aerosol-forming substrate, located downstream of the hollow tube is less likely to reach its combustion temperature than if it were located at the distal end of the heated aerosol-generating article. Furthermore, a pierceable film helps prevent air from being drawn through the rod. Thus, the risk of inadvertent or unintended ignition of the aerosol-forming substrate is reduced.

Preferably the hollow tube is a rigid hollow tube formed from a polymer, a metal or a ceramic. The rigid hollow tube is preferably formed from a material selected from the list consisting of metal foil, ceramic, highly filled paper, cellulose acetate and Polyaryletherketone (PAEK) polymer.

The aerosol-forming article may be a smoking article. During operation a smoking article containing the aerosol-forming substrate may be partially contained within the aerosol-generating device.

The smoking article may be substantially cylindrical in shape. The smoking article may be substantially elongate. The smoking article may have a length and a circumference substantially perpendicular to the length. The aerosol-forming substrate may be substantially cylindrical in shape. The aerosol-forming substrate may be substantially elongate. The aerosol-forming substrate may also have a length and a circumference substantially perpendicular to the length.

The smoking article may have a total length between approximately 30 mm and approximately 100 mm. The smoking article may have an external diameter between approximately 5 mm and approximately 12 mm. The smoking article may comprise a filter plug. The filter plug may be located at a downstream end of the smoking article. The filter plug may be a cellulose acetate filter plug. The filter plug is approximately 7 mm in length in one embodiment, but may have a length of between approximately 5 mm to approximately 10 mm.

In one embodiment, the smoking article has a total length of approximately 45 mm. The smoking article may have an external diameter of approximately 7.2 mm. Further, the aerosol-forming substrate may have a length of approximately 10 mm. Alternatively, the aerosol-forming substrate may have a length of approximately 12 mm. Further, the diameter of the aerosol-forming substrate may be between approximately 5 mm and approximately 12 mm. The smoking article may comprise an outer paper wrapper. Further, the smoking article may comprise a separation between the aerosol-forming substrate and the filter plug. The separation may be approximately 18 mm, but may be in the range of approximately 5 mm to approximately 25 mm.

The aerosol-forming substrate may be a solid aerosol-forming substrate. Alternatively, the aerosol-forming substrate may comprise both solid and liquid components. The aerosol-forming substrate may comprise a tobacco-containing material containing volatile tobacco flavour compounds which are released from the substrate upon heating. Alternatively, the aerosol-forming substrate may comprise a non-tobacco material. The aerosol-forming substrate may further comprise an aerosol former that facilitates the formation of a dense and stable aerosol. Examples of suitable aerosol formers are glycerine and propylene glycol.

If the aerosol-forming substrate is a solid aerosol-forming substrate, the solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco, cast leaf tobacco and expanded tobacco. The solid aerosol-forming substrate may be in loose form, or may be provided in a suitable container or cartridge. Optionally, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

As used herein, homogenised tobacco refers to material formed by agglomerating particulate tobacco. Homogenised tobacco may be in the form of a sheet. Homogenised tobacco material may have an aerosol-former content of greater than 5% on a dry weight basis. Homogenised tobacco material may alternatively have an aerosol former content of between 5% and 30% by weight on a dry weight basis. Sheets of homogenised tobacco material may be formed by agglomerating particulate tobacco obtained by grinding or otherwise combining one or both of tobacco leaf lamina and tobacco leaf stems. Alternatively, or in addition, sheets of homogenised tobacco material may comprise one or more of tobacco dust, tobacco fines and other particulate tobacco by-products formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco; alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof.

Optionally, the solid aerosol-forming substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

In a particularly preferred embodiment, the aerosol-forming substrate comprises a gathered crimpled sheet of homogenised tobacco material. As used herein, the term 'crimped sheet' denotes a sheet having a plurality of substantially parallel ridges or corrugations. Preferably, when the aerosol-generating article has been assembled, the substantially parallel ridges or corrugations extend along or parallel to the longitudinal axis of the aerosol-generating article. This advantageously facilitates gathering of the crimped sheet of homogenised tobacco material to form the aerosol-forming substrate. However, it will be appreciated that crimped sheets of homogenised tobacco material for inclusion in the aerosol-generating article may alternatively or in addition have a plurality of substantially parallel ridges or corrugations that are disposed at an acute or obtuse angle to the longitudinal axis of the aerosol-generating article when the aerosol-generating article has been assembled. In certain embodiments, the aerosol-forming substrate may comprise a gathered sheet of homogenised tobacco material that is substantially evenly textured over substantially its entire surface. For example, the aerosol-forming substrate may comprise a gathered crimped sheet of homogenised tobacco material comprising a plurality of substantially parallel ridges or corrugations that are substantially evenly spaced-apart across the width of the sheet.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

The aerosol-generating system is a combination of an aerosol-generating device and one or more aerosol-generating articles for use with the device. However, aerosol-generating system may include additional components, such as for example a charging unit for recharging an on-board electric power supply in an electrically operated or electric aerosol-generating device.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

The invention will be further described, by way of example only, with reference to the accompanying drawings in which.

Figure 1:
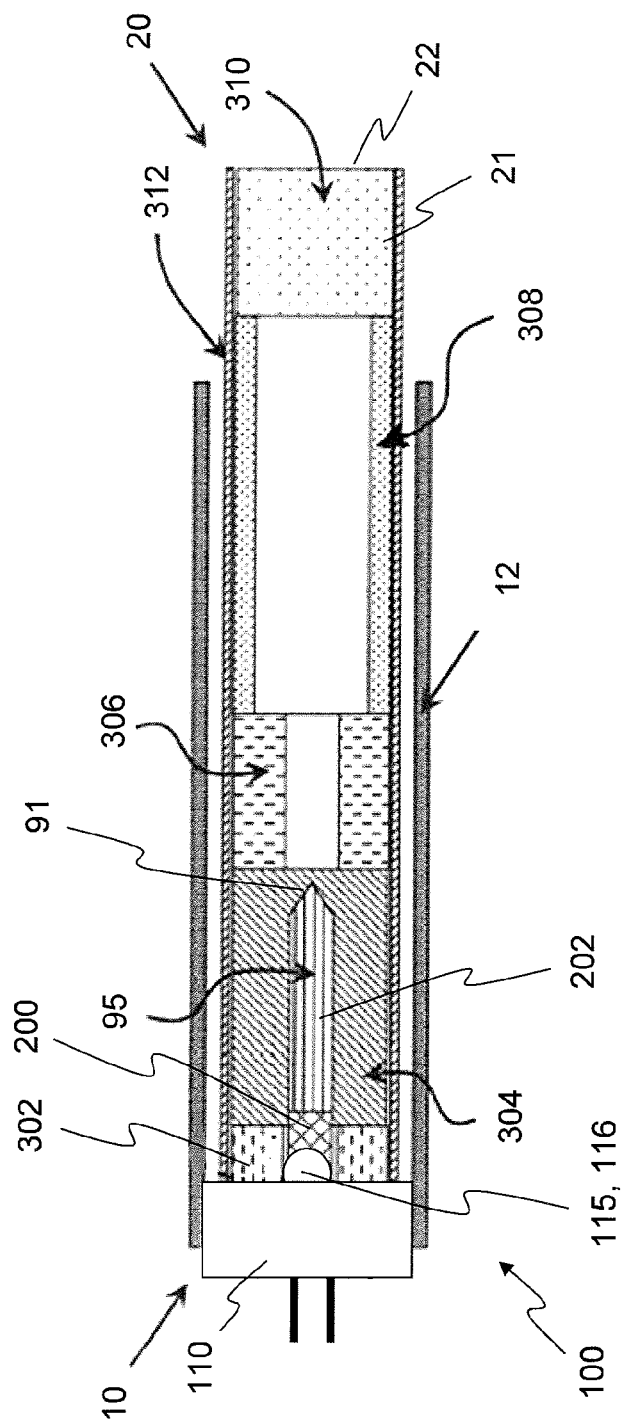
FIG. 1 shows a portion of an embodiment of an aerosol-generating device comprising a heating element module.

FIG. 1 illustrates a portion of an embodiment of an aerosol-generating device 10 comprising a heating element module 100. The aerosol-generating device 10 is illustrated in engagement with an aerosol-generating article 20 for consumption of the aerosol-generating article 20 by a user.

The aerosol-generating device 10 comprises an elongated sheath 12 for receiving an aerosol-generating article 20 for consumption. A proximal end 13 of the sheath 12 is open to allow access to the aerosol-generating article 20. A distal end 14 of the sheath 14 is spanned by a heating element module 100 comprising a heating element 95. The heating element 95 is retained by a heating element mount 110 such that a heating portion of the heating element 95 is located within the sheath 12. The heating portion is positioned to engage with a distal end of the aerosol-generating article when the aerosol-generating article 20 is fully received within the sheath 12.

The heating element 95 is shaped in the form of a blade terminating in a point 91. That is, the heating element 95 has a length dimension that is greater than its width dimension, which is greater than its thickness dimension. First and second faces 97, 98 of the heating element 95 are defined by the width and length of the heating element. First and second projections 115, 116 extend upwardly from a first surface of the mount 110. These first and second projections 115, 116 respectively abut the first and second faces 97, 98 of the heating element 95. The projections 115,116 act to stabilise the heating element 95 against stresses caused by deflection and torsion of the heating element 95. Table 1.0 below shows the comparison of the deflection and force required for failure between a heating element without the stabilising projections and with the stabilising projections. The test utilises an Instron 5565 material testing system. The test machine is configured to apply a force perpendicular to the heating element, adjacent the point 91, using a wedge shaped test head. The test head is lowered at a rate of approximately 0.1 mm per minute, and the initial load applied to the heating portion was 0.1 N. As can be seen from the test data shown in Table 1.0, the test was repeated 5 times for each type of heating element. The heating element of the present invention is shown to have a greater resistance to force before failure, a reduction in the deflection, and a reduction in the flexural stress.

TABLE 1.0

| Heating element type | Test no. | Thickness (mm) | Width (mm) | Fracture force (N) | Deflection (mm) | Flexural stress (Mpa) |
|---|---|---|---|---|---|---|
| Heating Element with the stabilising projections | 1 | 0.40 | 4.90 | 5.3 | 1.50 | 487 |
| | 2 | 0.38 | 4.86 | 5.4 | 1.50 | 554 |
| | 3 | 0.39 | 4.87 | 5.2 | 1.30 | 505 |
| | 4 | 0.40 | 4.78 | 5.4 | 1.30 | 508 |
| | 5 | 0.39 | 4.94 | 6.0 | 1.40 | 575 |
| Average | | 0.39 | 4.87 | 5.5 | 1.40 | 526 |
| STD | | 0.01 | 0.06 | 0.3 | 0.10 | 37 |
| Heating element without the stabilising projections | 1 | 0.40 | 4.82 | 5.6 | 1.80 | 523 |
| | 2 | 0.37 | 4.88 | 5.3 | 1.40 | 571 |
| | 3 | 0.37 | 4.92 | 5.2 | 1.50 | 556 |
| | 4 | 0.36 | 4.90 | 5.0 | 1.40 | 567 |
| | 5 | 0.37 | 4.88 | 5.0 | 1.30 | 539 |
| Average | | 0.37 | 4.88 | 5.2 | 1.48 | 551 |
| STD | | 0.02 | 0.04 | 0.2 | 0.19 | 20 |

The heating element comprises two heating portions 200 and 202. The heating portion 200 is adjacent the first and second projections 115, 116 has an electrical resistance less than the electrical resistance of the heating portion 202. In use, this means that the heating portion 202 is heated to a higher temperature than the heating portion 200, the current in each portion being the same.

The aerosol-generating device 10 comprises a power supply and electronics (not shown) that allow the heating element 95 to be actuated. Such actuation may be manually operated or may occur automatically in response to a user drawing on the aerosol-generating article.

An exemplary aerosol-generating article, as illustrated in FIG. 1, can be described as follows.

The article 20 comprises five elements, a rigid hollow tube 302, an aerosol-forming substrate 304, a hollow cellulose acetate tube 306, a transfer section 308, and a mouthpiece filter 310. These five elements are arranged sequentially and in coaxial alignment and are assembled by a cigarette paper 312 to form a rod. When assembled, the article 20 may be between 45 millimetres and 52 millimetres long, and has a diameter of 7.2 millimetres.

The rigid hollow tube 302 is a ceramic tube having a length of 7 millimetres.

The aerosol-forming substrate 304 is located downstream of the rigid hollow tube 302 and comprises a bundle of crimped cast-leaf tobacco wrapped in a filter paper. The cast-leaf tobacco includes additives, including glycerine as an aerosol-forming additive.

The cellulose acetate tube 306 is located immediately downstream of the aerosol-forming substrate 304 and is formed from cellulose acetate. The tube 306 defines an aperture having a diameter of 3.3 millimetres. One function of the tube 306 is to locate the aerosol-forming substrate 304 towards the distal end of the article 20 so that it can be contacted with a heating element. The tube 306 acts to prevent the aerosol-forming substrate 304 from being forced along the article 20 towards the mouth-end when a heating element is inserted.

The transfer section 308 comprises a thin-walled tube of 18 millimetres in length. The transfer section 308 allows volatile substances released from the aerosol-forming substrate 304 to pass along the article 20 towards the mouth end 20. The volatile substances may cool within the transfer section 308 to form an aerosol. An aerosol-cooling element, such as a crimped and gathered sheet of polylactic acid may be used instead of the transfer section.

The mouthpiece filter 310 is a conventional mouthpiece filter formed from cellulose acetate, tow and having a length of 7 millimetres.

The five elements identified above are assembled by being tightly wrapped within a cigarette paper 312. The paper in this specific embodiment is a standard cigarette paper having standard properties or classification. The paper in this specific embodiment is a conventional cigarette paper.

As the aerosol-generating article 20 is pushed into the sheath 12 the point 91 of the heating element 95 engages with the aerosol-forming substrate 304. By applying a force to the aerosol-generating article, the second heating portion 202 penetrates into the aerosol-forming substrate 304. When the aerosol-generating article 20 is properly engaged with the aerosol-generating device 10, the second heating portion 202 has been inserted into the aerosol-forming substrate 304. When the heating element 95 is actuated, the aerosol-forming substrate 30 is warmed and volatile substances are generated or evolved. As a user draws on the mouth end of the aerosol-generating article 20, air is drawn into the aerosol-generating article and the volatile substances condense to form an inhalable aerosol. This aerosol passes through the mouth-end 22 of the aerosol-generating article and into the user's mouth.

Figure 2:
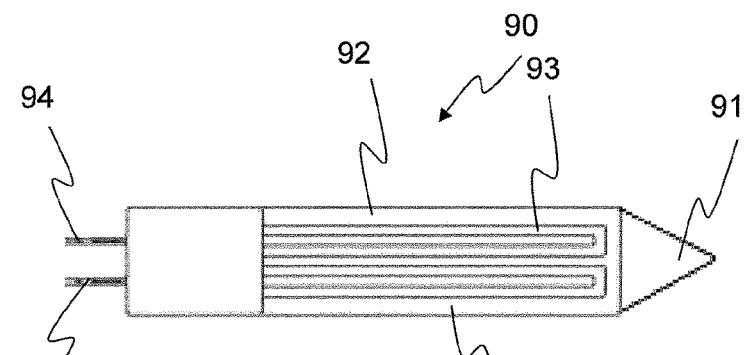
FIG. 2 shows a detailed plan view of a heating element component of the heating element module shown in FIG. 1.

FIG. 2 illustrates a heating element 90 component of a heating element module 100 in greater detail. The heating element 90 is substantially blade-shaped. That is, the heating element has a length that in use extends along the longitudinal axis of an aerosol-generating article engaged with the heating element, a width and a thickness. The width is greater than the thickness. The heating element 90 terminates in a point or spike 91 for penetrating an aerosol-generating article 20. The heating element 90 comprises an electrically insulating substrate 92, which defines the shape of the heating element 90. The electrically insulating material may be, for example, alumina (Al2O3), stabilized zirconia (ZrO2). It will be apparent to one of ordinary skill in the art that the electrically insulating material may be any suitable electrically insulating material and that many ceramic materials are suitable for use as the electrically insulating substrate.

Tracks 93 of an electrically conductive material are plated on a surface of the insulating substrate 92. The tracks 93 are formed from a thin layer of platinum. Any suitable conductive material may be used for the tracks, and the list of suitable materials includes many metals, including gold, that are well known to the skilled person. One end of the tracks 93 is coupled to a power supply by a first contact 94, and the other end of the tracks 93 is coupled to a power supply by a second contact 96. When a current is passed through the tracks 93, resistive heating occurs. This heats the entire heating element 90 and the surrounding environment. When a current passing through the tracks 93 of the heating element 90 is switched off, there is no resistive heating and the temperature of the heating element 90 is swiftly lowered.

Figure 3:
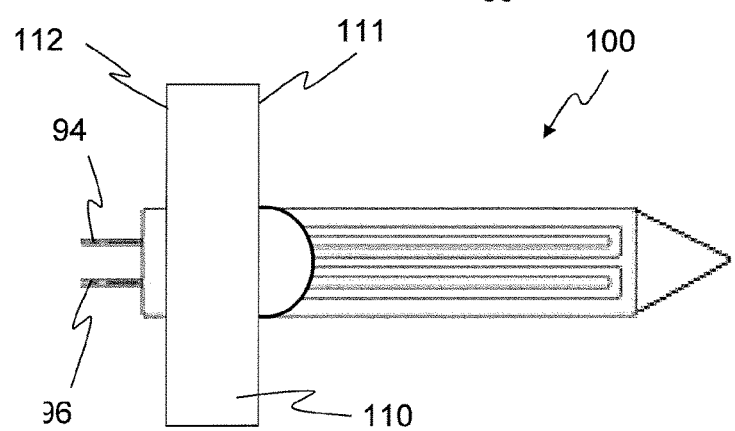
FIG. 3 shows a detailed plan view of the heating element module shown in FIG. 1.
Figure 4:
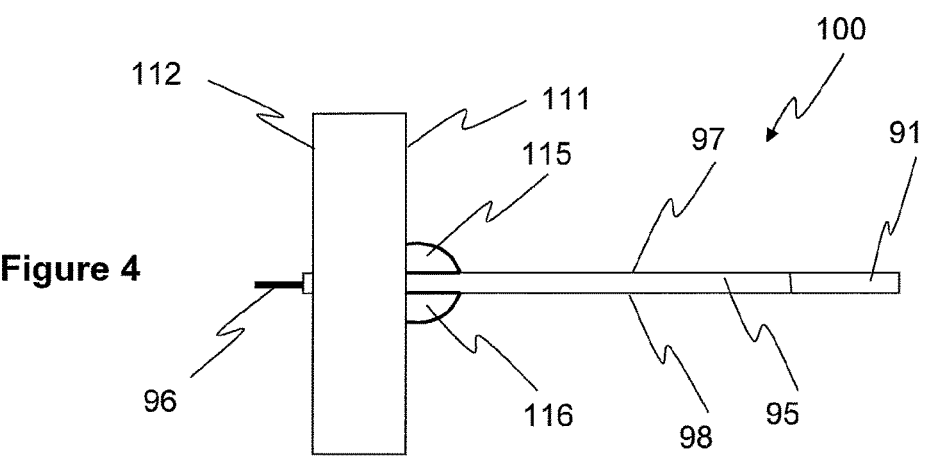
FIG. 4 shows a side view of the heating element module shown in FIG. 3.
Figure 5:
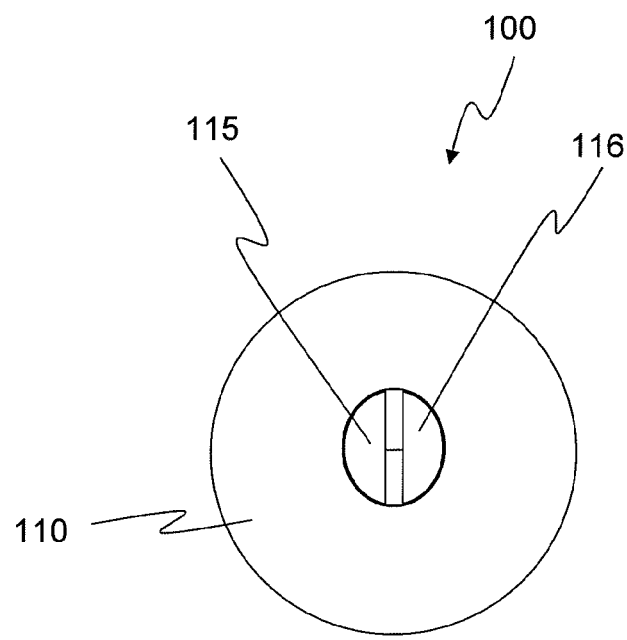
FIG. 5 shows an end view of the heating element module shown in FIGS. 3 and 4.

FIGS. 3, 4, and 5 illustrate a heating element module 100 comprising a heating element 90 mounted in a heating element mount 110. The heating element 90 is mounted through a polymeric mount 110. A heating portion 95 of the heating element 90 extends perpendicularly from a first surface 111 of the heating element mount 110. A rear portion of the heating element 90, including the electrical contacts 94, 96 extends perpendicularly from a second surface 112 of the mount 110. The mount 110 retains the heating element 90 firmly in place. Two dome-shaped projections extend perpendicularly from the first surface 111 of the mount 110. These projections abut first 97 and second 98 faces of the heating portion 95 of the heating element 90. When incorporated in an aerosol-generating device (for example as illustrated in FIG. 1) the heating element module locates the heating portion 95 of the heating element 90 within the sheath 12 for contact with an aerosol-generating article.

Figure 6:
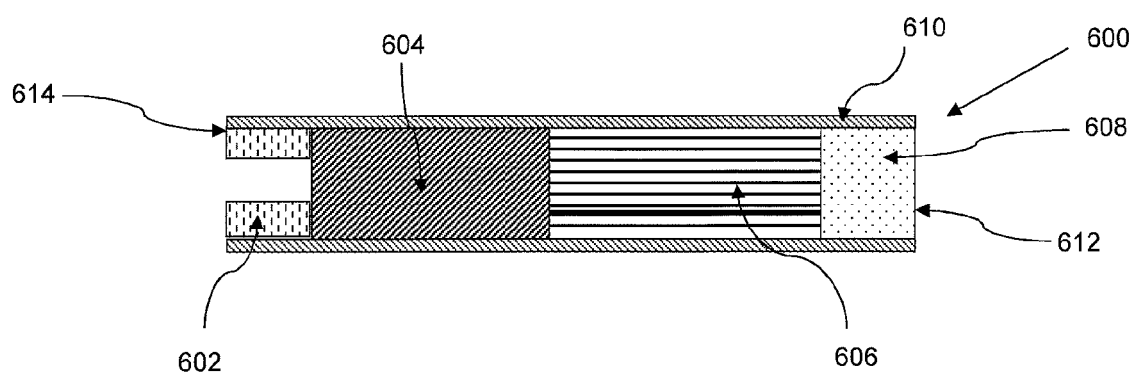
FIG. 6 shows a schematic of an aerosol-generating article of ruse in an aerosol-generating device.

FIG. 6 illustrates an alternative heated aerosol-generating article 600 which may be used with the aerosol-generating device as described above. The aerosol-generating article 600 comprises four elements arranged in coaxial alignment: a rigid hollow tube 602, an aerosol-forming substrate 604, an aerosol-cooling element 606, and a mouthpiece 608. These four elements are arranged sequentially and are circumscribed by an outer wrapper 610 to form the heated aerosol-generating article 600. The aerosol-generating article 600 has a proximal or mouth end 612, which a user inserts into his or her mouth during use, and a distal end 614 located at the opposite end of the aerosol-generating article 600 to the mouth end 612.

The distal end 614 of the aerosol-generating article may also be described as the upstream end of the aerosol-generating article 600 and the mouth end 612 of the aerosol-generating article 600 may also be described as the downstream end of the aerosol-generating article 600. Elements of the aerosol-generating article 600 located between the mouth end 612 and the distal end 614 can be described as being upstream of the mouth end 612 or, alternatively, downstream of the distal end 614.

The rigid hollow tube 602 is located at the extreme distal or upstream end of the aerosol-generating article 600. In the article shown in FIG. 6, the rigid hollow tube 602 is a hollow ceramic tube. This rigid hollow tube 602 may protect the aerosol-forming substrate from flames applied to the distal end of the article 600, thereby providing a means of reducing the chance of inadvertent ignition.

In the article illustrated in FIG. 6, the aerosol-forming substrate 604 comprises a gathered sheet of crimped homogenised tobacco material circumscribed by a wrapper. The crimped sheet of homogenised tobacco material comprises comprising glycerine as an aerosol-former.

The aerosol-cooling element 606 is located immediately downstream of the aerosol-forming substrate 604 and abuts the aerosol-forming substrate 604. In use, volatile substances released from the aerosol-forming substrate 604 pass along the aerosol-cooling element 606 towards the mouth end 612 of the aerosol-generating article 600. The volatile substances may cool within the aerosol-cooling element 606 to form an aerosol that is inhaled by the user. In the article illustrated in FIG. 6, the aerosol-cooling element comprises a crimped and gathered sheet of polylactic acid circumscribed by a wrapper. The crimped and gathered sheet of polylactic acid defines a plurality of longitudinal channels that extend along the length of the aerosol-cooling element 606.

The mouthpiece 608 is located immediately downstream of the aerosol-cooling element 606 and abuts the aerosol-cooling element 606. In the article illustrated in FIG. 6, the mouthpiece 608 comprises a conventional cellulose acetate tow filter of low filtration efficiency.

To assemble the aerosol-generating article 600, the four elements described above are aligned and tightly wrapped within the outer wrapper 610. In some embodiments, a distal end portion of the outer wrapper 610 of the aerosol-generating article 600 may be circumscribed by a band of tipping paper.

The aerosol-generating article 600 illustrated in FIG. 6 is designed to engage with an aerosol-generating device comprising a heating element in order to be smoked or consumed by a user. In use, the heating element of the aerosol-generating device heats the aerosol-forming substrate 604 of the aerosol-generating article 600 to a sufficient temperature to form an aerosol, which is drawn downstream through the aerosol-generating article 600 and inhaled by the user.

The invention claimed is:

1. A heating element module for an aerosol-generating device, comprising:
    an elongate heating element having a heating portion;
    a heating element mount, wherein the elongate heating element extends substantially perpendicularly from a first surface of the heating element mount; and
    first and second projections extending substantially perpendicularly from the first surface of the heating element mount and abutting first and second sides of the elongate heating element, wherein portions of the first and the second projections abutting the first and the second sides of the elongate heating element are configured to freely slide relative to the elongate heating element.

2. The heating element module according to claim 1, wherein a portion of the elongate heating element extending from the first surface of the heating element mount has a length that is greater than a width thereof, which is greater than a thickness thereof, and
    wherein the first and second sides of the elongate heating element are faces defined by the width and the length.

3. The heating element module according to claim 1, wherein the first and second projections extend from the first surface of the heating element mount for a distance of between 2 mm and 10 min along the length of the elongate heating element.

4. The heating element module according to claim 1, wherein each of the first and second projections has a non-planar free surface.

5. The heating element module according to claim 4, wherein the non-planar free surface is spherical.

6. The heating element module according to claim 1, wherein the heating portion comprises a ceramic insulating substrate supporting tracks formed from an electrically conductive material.

7. The heating element module according to claim 1, further comprising electrical contacts configured to supply power to the heating portion, wherein the electrical contacts extend from a second surface of the heating element mount.

8. The heating element module according to claim 1, the elongate heating element further comprising a heater substrate, and the heating portion further comprising a first portion and a second portion configured such that, when an electrical current is passed through the heating portion, the first portion is heated to a higher temperature than the second portion,
    wherein the first portion of the heating portion is disposed on a heating area of the heater substrate, and the second portion of the heating portion is disposed on a holding area of the heater substrate, and
    wherein the heating element mount and the first and second projections are adjacent the holding area of the heater substrate.

9. The heating element module according to claim 8, wherein the second portion of the heating portion is longer than the first portion.

10. An aerosol-generating device, comprising:
    an elongate cavity configured to receive an aerosol-generating article; and
    a heating element module comprising:
        an elongate heating element having a heating portion,
        a heating element mount, wherein the elongate heating element extends substantially perpendicularly from a first surface of the heating element mount, and
        first and second projections extending substantially perpendicularly from the first surface of the heating element mount and abutting first and second sides of the elongate heating element, wherein portions of the first and the second projections abutting the first and the second sides of the elongate heating element are configured to freely slide relative to the elongate heating element,
    wherein the heating portion of the elongate heating element is configured to extend into the elongate cavity such that it is insertable into an aerosol-generating article received in the elongate cavity.

* * * * *